United States Patent [19]

Matsumoto et al.

[11] 4,299,997

[45] Nov. 10, 1981

[54] PROCESS FOR PRODUCING ETHYLENE GLYCOL MONO-TERT-BUTYL ETHER

[75] Inventors: Tadashi Matsumoto; Osamu Kuratani; Yasunori Hirose, all of Soka; Susumu Toba, Saitama, all of Japan

[73] Assignee: Maruzen Oil Co., Ltd., Osaka, Japan

[21] Appl. No.: 105,000

[22] Filed: Dec. 18, 1979

Related U.S. Application Data

[63] Continuation-in-part of Ser. No. 70,761, Aug. 30, 1979, abandoned.

[30] Foreign Application Priority Data

Aug. 30, 1978 [JP] Japan ................................. 53/105814

[51] Int. Cl.$^3$ ............................................. C07C 41/06
[52] U.S. Cl. .................................... 568/678; 568/697; 568/672
[58] Field of Search ............... 568/678, 672, 697, 694, 568/895, 896, 899

[56] References Cited

U.S. PATENT DOCUMENTS 2,480,940  6/1949  Leum et al. ......................... 568/697

FOREIGN PATENT DOCUMENTS 2450667  4/1975  Fed. Rep. of Germany ...... 568/678
5129413  3/1976  Japan .................................... 568/678
 957000  4/1964  United Kingdom ................ 568/697

*Primary Examiner*—Howard T. Mars
*Attorney, Agent, or Firm*—Sughrue, Mion, Zinn, Macpeak and Seas

[57] ABSTRACT

An improved process for producing ethylene glycol mono-tert-butyl ether by reacting ethylene glycol with isobutylene in the presence of a catalyst of strongly acidic cation-exchange material is disclosed which enables the production of ethylene glycol mono-tert-butyl ether in a high yield while suppressing the formation of by-product ethylene glycol di-tert-butyl ether by previously adding ethylene glycol di-tert-butyl ether to the reaction system and conducting the reaction at temperatures of about 60 to 130° C.

16 Claims, 1 Drawing Figure

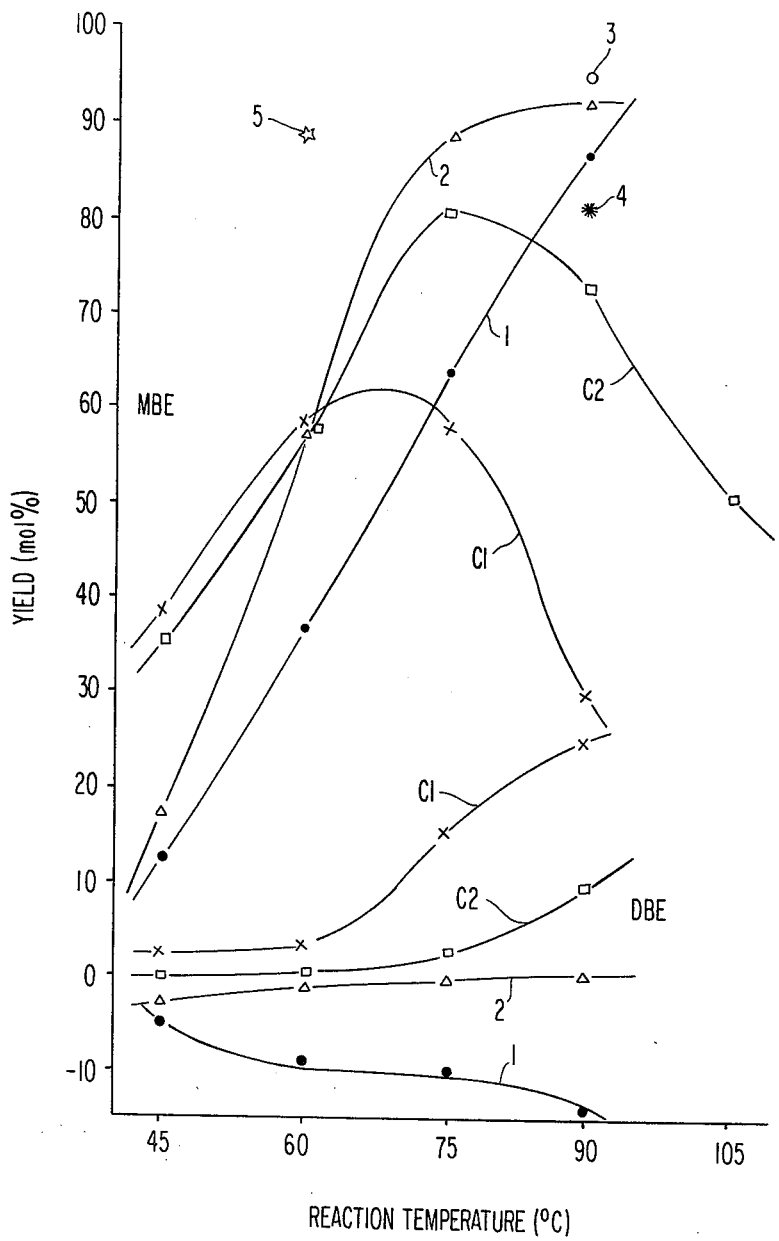

PROCESS FOR PRODUCING ETHYLENE GLYCOL MONO-TERT-BUTYL ETHER

CROSS-REFERENCE TO RELATED APPLICATIONS

This application is a continuation in-part of U.S. Application Ser. No. 70,761, filed on Aug. 30, 1979, now abandoned.

BACKGROUND OF THE INVENTION

1. Field of the Invention

This invention relates to a process for producing ethylene glycol mono-tert-butyl ether from ethylene glycol and isobutylene and, more particularly, to a process of conducting the above-described reaction by adding ethylene glycol di-tert-butyl ether to the reaction system.

2. Description of the Prior Art

Ethylene glycol mono-tert-butyl ether is a useful material exhibiting excellent properties as a solvent, dispersing agent, diluent, or the like in the field of paints and ink. It is well known that ethylene glycol mono-tert-butyl ether can be synthesized from isobutylene and ethylene glycol by reacting them in the presence of an acid catalyst. In addition, it is also known from, for example, U.S. Pat. No. 3,317,483, 3,170,000, 2,480,940, Japanese Patent Application (OPI) No. 82004/75 (The term "OPI" as used herein refers to a "published unexamined Japanese patent application") that strongly acidic cation-exchange materials are effective as the catalysts.

However, in producing ethylene glycol mono-tert-butyl ether from isobutylene and ethylene glycol, the use of these catalysts has failed to eliminate formation of an ethylene glycol di-tert-butyl ether by-product. Formation of the by-product ethylene glycol di-tert-butyl ether (abbreviated DBE) results in reduction in the yield of ethylene glycol mono-tert-butyl ether (abbreviated MBE), which is economically disadvantageous for the production of the end product. Thus, it has been desired to develop a process of suppressing formation of the by-product di-tert-butyl ether.

No processes have so far been discovered which effectively suppress formation of the by-product DBE in the etherification reaction between isobutylene and ethylene glycol.

As indicated above, three U.S. Patents teach that ethylene glycol mono-tert-butyl ether can be synthesized from ethylene glycol and isobutylene. Of these, U.S. Pat. No. 3,170,000 relates to a process of producing MBE from an olefin mixture containing isobutylene and alcohol, and selectively separating and recovering tert-olefin by the decomposition of the resulting MBE. This patent describes recycling a mixture of alcohol and MBE obtained in the final step to an etherification reactor in the first step. Also, Japanese Patent Application (OPI) No. 29413/76 describes the process of producing ethylene glycol mono-tert-butyl ether from ethylene glycol and isobutylene by previously adding ethylene glycol mono-tert-butyl ether to the reaction system. However, these processes suffer from the problem that the amount of by-product ethylene glycol di-tert-butyl ether further increases.

SUMMARY OF THE INVENTION

A primary object of the present invention is to produce an end product of ethylene glycol mono-tert-butyl ether in a good yield while suppressing formation of the by-product of ethylene glycol di-tert-butyl ether.

Another object of the present invention is to provide a process which enables the production of end product MBE at a fast reaction rate while effectively suppressing formation of the by-product ethylene glycol di-tert-butyl ether even when an elevated reaction temperature is employed.

A process to which the present invention is applicable is for producing ethylene glycol mono-tert-butyl ether by reacting ethylene glycol with isobutylene in the presence of a strongly acidic cation-exchange material. According to the present invention, ethylene glycol mono-tert-butyl ether can be produced by previously adding an additive comprising ethylene glycol di-tert-butyl ether to the reaction system and employing a reaction temperature of about 60° to 130° C.

BRIEF DESCRIPTION OF THE DRAWING

The FIGURE is a graph showing the yield of ethylene glycol mono-tert-butyl ether (MBE) (mol% based on isobutylene) (plotted on the ordinate) and the amount of the by-product of ethylene glycol di-tert-butyl ether (DBE) (mol% based on isobutylene) (plotted on the ordinate) in the reaction between the ethylene glycol and isobutylene in the presence of a strongly acidic cation-exchange material catalyst versus reaction temperature (plotted as abscissa).

In the FIGURE, curves 1–2, and points 3–5 respectively show the results in Examples 1–5 described below, and curves C1–C2 respectively show the results in Comparative Examples 1 and 2 described below. Curve 1 and points 3 and 5 shown the results of the cases of adding ethylene glycol di-tert-butyl ether as an additive previously added to the reaction system, and curve 2 and point 4 show the results of the cases of adding a mixture of ethylene glycol di-tert-butyl ether and ethylene glycol mono-tert-butyl ether as the additive. Curves 1, 2 and point 4 show the results of reacting for 1 hour, point 3 for 3 hours, and point 5 for 4 hours. Curve C1 shows the results of the case of adding only ethylene glycol mono-tert-butyl ether as the additive, whereas curve C2 shows the results of the case of adding no additives, with the reaction time being 1 hour in both cases.

Comparison of the results of curves 1, 2, C1 and C2, which were conducted under the same reaction conditions except for additives reveals that formation of the by-product of ethylene glycol di-tert-butyl ether is effectively suppressed and the yield of the end product of ethylene glycol mono-tert-butyl ether is maintained at a high level in Examples 1 and 2 in accordance with the present invention.

DETAILED DESCRIPTION OF THE INVENTION

As a result of detailed investigations of the reaction between ethylene glycol and isobutylene, it has been discovered that the reaction is unexpectedly sensitive to temperature, and that materials copresent in the reaction system clearly influence the reaction in a different manner in a low reaction temperature (not higher than 60° C.) than in a high reaction temperature (not lower than 60° C.).

That is, it has been found that, when the reaction is conducted at various temperatures within the range of 45° to 130° C. by pre-adding DBE to the reaction system so as to suppress formation of the DBE, the addition of DBE completely suppressed formation of the by-product of DBE over the entire temperature range. Although the yield of the end product MBE was less in the lower temperature range when pre-adding DBE as compared with the case of not adding the additive, as the temperature increased, the addition of DBE served to increase the yield of end product MBE as compared with the case of not adding DBE. In this reaction, however, the net yield of DBE in some cases is negative, though it depends upon the the amount of DBE added, and hence it is sometimes necessary to separately prepare the DBE added at the beginning of the reaction.

When the same tests as described above were conducted by adding a mixture of DBE and MBE so as to remove the above-described defect, formation of the by-product DBE was suppressed to almost zero over the entire temperature range, the yield of MBE improved with an increase in reaction temperature.

As stated above, the addition of DBE alone and the addition of the mixture of DBE and MBE tends to increase MBE yield, with the mixture providing the higher MBE yield. Thus, it might be expected that addition of MBE alone would further increase the yield of MBE and suppress the amount of by-product DBE. With this in mind, the effects of the addition of MBE alone were also tested in the same manner as described above. In this case, however, it was found that as the reaction temperature increased, the amount of the by-product DBE seriously increased. At reaction temperatures of about 60° C. or above, the yield of MBE reached a maximum unexpectedly at about 70° C., and at higher reaction temperatures the yield of MBE sharply decreased.

Thus, the addition of DBE to the reaction system provides results substantially different from the results provided by the addition of MBE at different reaction temperature and in the case of adding a mixture of DBE and MBE the DBE in the mixture is a dominant factor in both the formation of MBE and suppressing the formation of by-product DBE.

The relationship between reaction temperature and yield of MBE can be explained in more detail by referring to the accompanying FIGURE. The addition of MBE (C1) provides the best results in the tests of reacting for 1 hour at a temperature not higher than 60° C., whereas at a temperature higher than 60° C., the addition of no additives (C2) or the addition of a mixture of DBE and MBE (2 ) provides results which are better than the addition of MBE along (C1). The MBE yield in the case of adding DBE alone (1) reaches about 40% at about 60° C., which is high enough to make production practical.

At 75° C. the MBE yield with the addition of DBE (1) reaches as high as about 60% and exceeds the yield with the addition of MBE (C1).

Further, in the test at about 85° C. or above, the addition of DBE (1) provides better yields than the yield without additives (C2) and substantially the same results as those with a mixture of MBE and DBE (2), with the yield of MBE reaching about 90%. Additionally, in the case of no additives (C2), the yield of MBE reaches a maximum at about 75° C. and, as the reaction temperature exceeds 75° C., the yield of MBE sharply decreases, whereas in the case of adding MBE alone (C1), the yield of MBE reaches a maximum at about 65° to 70° C. and sharply decreases at reaction temperatures higher than that.

The amount of the by-product DBE can be effectively suppressed by pre-adding to the reaction system DBE (1) or a mixture of DBE and MBE (2) according to the present invention as compared with the case of pre-adding MBE (C1) or no additives (C2) to the reaction system.

The process of the present invention of reacting ethylene glycol with isobutylene to produce ethylene glycol mono-tert-butyl ether may be carried out by recycling essentially pure by-product DBE separated from the reaction mixture containing mostly ethylene glycol mono-tert-butyl ether and a slight amount of the by-product ethylene glycol di-tert-butyl ether through distillation, extraction, or like means. However, as has been stated before, ethylene glycol di-tert-butyl ether added in the process of the present invention need not be pure and, when a mixture containing MBE is used, the reaction proceeds with the DBE functioning as the dominant factor, thus much better results are obtained. In addition, separation of ethylene glycol di-tert-butyl ether and ethylene glycol mono-tert-butyl ether as a mixture from the reaction product is generally easier than separation of the by-product of ethylene glycol di-tert-butyl ether alone (because the monoether and the diether form an azeotrope), and hence addition of ethylene glycol di-tert-butyl ether containing ethylene glycol mono-tert-butyl ether to the reaction system is industrially preferred.

In the practice of the process of the present invention, the reaction is not substantially inhibited by the presence of by-products, additives, and the like, in the reaction of producing MBE from isobutylene and ethylene glycol, such as diisobutylene, triisobutylene, water, etc. When water is present, tertiary butyl alcohol is produced as a by-product. In the present invention, the reaction can be carried out by adding a large amount of water (the preferred molar ratio of water to the isobutylene is 1:0.1 to 1:10) into the reaction system. In this case, the etherification reaction and the hydration reaction are simultaneously caused, and as a result, tert-butyl alcohol is produced together with ethylene glycol mono-tert butyl ether. Also, needless to say, ethylene glycol di-tert-butyl ether used in the present invention is not necessarily limited to that produced by the reaction between isobutylene and ethylene glycol, and ethylene glycol di-tert-butyl ether produced from other starting materials or according to other reaction pathway may also be used.

Isobutylene used in the process of the present invention may be isobutylene itself or a $C_4$ fraction comprising a mixture of hydrocarbons containing 4 carbon atoms (e.g., a mixture of isobutylene, n-butylene, butanes, etc.) obtained by naphtha thermal cracking, catalytic cracking of kerosene and light oil, or the like. In the case of using such mixture, isobutylene reacts selectively.

Strongly acidic cation-exchange materials used in the process of the present invention as a catalyst are water-insoluble materials having a strong acidity, namely sulfonated materials having a sulfonic acid group ($SO_3H$) as a functional group. As the strongly acidic cation-exchange materials, there are illustrated styrene sulfonic acid type cation-exchange resins, phenolsulfonic acid type cation-exchange resins, sulfonated coal, sulfonated asphalt, etc. The styrene sulfonic acid type cation-exchange resins are prepared by sulfonating resins of copolymers of styrene and a poly-unsaturated compound like divinylbenzene (commercially available as Amberlyst 15, Amberlite IR-118, and Amberlite IR-120 made by Rohm & Haas Co., Dowex 50W-X12 made by Dow Chemical Co., etc.). The phenolsulfonic acid type cation-exchange resins are usually prepared by condensing phenolsulfonic acid with formaldehyde (commercially available as Amberlite IR-1, Amberlite IR-100 and Amberlite IR-105G made by Rohm & Haas Co., etc.). The sulfonated coal is prepared by sulfonating bituminous coal with sulfuric acid (commercially available as Nalcite X and Nalcite AX made by Dow Chemical Co., Zeo-Karb H made by The Permutit Co., Ltd., Dursarit S made by Activit N.V., etc.). When these strongly acidic cation-exchange materials are obtained in neutralized form like a sodium salt, they must be treated with a strong inorganic acid like hydrochloric acid to activate to hydrogen exchange, then washed with water to remove sodium and chloride ions before use. As to the physical structure of these strongly acidic cation-exchange materials, either a gel type material having a small surface area or a macroporous type material having an enormous network structure and therefore having a large surface area may be used.

Low reaction temperatures result in a low yield of the MBE end product, whereas too high reaction temperatures (higher than 130° C.) thermally damage the catalytic activity of the ion-exchange material. Therefore, in the practice of the present invention, it is suitable to set the lower limit of the reaction temperature at about 60° C., preferably about 75° C., and the upper limit at about 130° C. in view of heat resistance of the catalyst of ion-exchange material, with about 85° to 110° C. being particularly preferred.

Reaction pressure is preferably high enough to maintain the reaction mixture in a liquid phase, but a reaction pressure permitting part of the reaction mixture to exist in a gas phase may also be employed. The reaction can be conducted under ordinary (atmospheric) pressure or an applied pressure. Usually the pressure is about 1 to 50 kg/cm$^2$.

The molar ratio of the starting ethylene glycol to the starting isobutylene is not particularly limited but is usually about 1:0.1 to 1:10, particularly about 1:0.3 to 1:5. The amount of ethylene glycol di-tert-butyl ether to be added is at least about 10 mol%, particularly preferably about 30 to 80 mol%, based on the ethylene glycol or isobutylene, whichever is less.

As has been described before, in the process of producing ethylene glycol mono-tert-butyl ether from isobutylene and ethylene glycol, the reaction conducted by adding only MBE to the reaction system results in an increased amount of the by-product of DBE and, when the reaction temperature becomes 60° C. or higher, there results a decreased yield of the MBE end product as compared with the case of no additives, and hence existence of a large content of MBE in the DBE added to the reaction system is not preferred. Therefore, the ratio of MBE to the DBE in the additive mixture is particularly preferably within the range of not more than about 3 mols of MBE per mol of DBE, through a ratio of about 5 mols of MBE per mol of DBE is still somewhat effective.

The amount of the cation-exchange material used as a catalyst is not particularly limited but it is usually about 5 to 30% by weight, preferably about 1 to 15% by weight based on the starting materials.

Usually, solvents are not necessary for conducting the reaction, but inert solvents such as hydrocarbons exemplified by n-heptane, n-hexane, benzene, toluene, xylene, or halogenated hydrocarbons exemplified by trichloroethylene, tetrachloroethane, tetrachloromethane may be used.

The reaction may be conducted in a batchwise manner under stirring or a continuous manner. In addition, it may be carried out in a flow method by passing the starting materials and additives through a fixed catalyst bed. The reaction time is not particularly limited, but a reaction time of about 5 minutes to 50 hours is suitable for the batchwise manner, with about 20 minutes to 10 hours being particularly preferred. In the case of conducting the reaction according to continuous flow method, a liquid hourly space velocity of total mixture of the starting materials and additive is suitably about 0.1 to 10 hr$^{-1}$, particularly preferably about 0.5 to 2 hr$^{-1}$. With the flow method, linear velocity of the total mixture of the starting materials and additive passing through the catalyst bed (flow amount of total mixture in cm$^3$/hr per cm$^2$ of cross-sectional area of the reactor, wherein said flow amount is represented as a liquid state at room temperature under pressure) is suitably about 30 cm/hr or more, particularly preferably about 60 cm/hr to 50 m/hr.

Separation of ethylene glycol mono-tert-butyl ether from the reaction mixture can be conducted according to ordinary methods such as distillation and/or solvent extraction using a solvent such as water, heptane, alcohol, etc., or extraction distillation.

When the reaction between ethylene glycol and isobutylene is conducted at high temperatures by adding ethylene glycol di-tert-butyl ether to the reaction system, formation of the by-product of ethylene glycol di-tert-butyl ether can effectively be suppressed and, at the same time, the end product of ethylene glycol mono-tert-butyl ether can be obtained in a high yield. In particular, unlike the teaching of U.S. Pat. No. 3,170,000 in which MBE-containing alcohol is fed to an etherifying reactor which results in an increased amount of the by-product of DBE and a decreased yield of the end product of MBE, the process of the present invention effectively suppresses formation of the DBE by-product even when high reaction temperatures are employed and, therefore, the reaction can be completed in a short time with a high yield of ethylene glycol mono-tert-butyl ether.

According to the present invention, the net increase in the amount of ethylene glycol di-tert-butyl ether can be made zero by recycling the by-produced ethylene glycol di-tert-butyl ether to the reactor, whereby all starting materials can be converted to ethylene glycol mono-tert-butyl ether.

The present invention will now be described in more detail by the following Examples and Comparative Examples which, however, are merely illustrative and should not be construed as limiting the process of the present invention.

EXAMPLE 1

5.25 g of Amberlyst 15 (Made by Rohm & Haas Co.; macroporous type resin; total exchange capacity: 4.9 meq/g-dry resin; specific surface area: 40–50 m$^2$/g; average pore size: 200–600 Å) as a catalyst and, as starting materials, 35.0 g (0.565 mol) of ethylene glycol, 11.7 g (0.209 mol) of isobutylene, and as an additive, 17.9 g (0.103 mol) of ethylene glycol di-tert-butyl ether were charged in an autoclave (200 ml in volume) equipped with a stirrer rotating at 1,300 rpm, followed by charging a nitrogen gas and reacting for 1 hour under a pressure of 20 kg/cm² at a predetermined reaction temperature. After completion of the reaction, isobutylene was discharged, and the remaining reaction product was analyzed according to gas chromatograph. The results thus obtained are tabulated in Table 1.

Ethylene glycol mono-tert-butyl ether was produced in a high yield, and the formation of ethylene glycol di-tert-butyl ether was effectively suppressed.

TABLE 1

| | Reaction Temperature (°C.) | | | |
|---|---|---|---|---|
| | 45 | 60 | 75 | 90 |
| Ethylene Glycol (mol) | | | | |
| Feed Amount (a) | 0.565 | 0.565 | 0.565 | 0.565 |
| Resulting Amount (b) | 0.549 | 0.506 | 0.452 | 0.413 |
| Yield (b-a) | −0.016 | −0.059 | −0.113 | −0.152 |
| Diisobutylene | | | | |
| Yield (mol) | 0.001 | 0.009 | 0.006 | 0.005 |
| DBE (mol) | | | | |
| Feed Amount (a) | 0.103 | 0.103 | 0.103 | 0.103 |
| Resulting Amount (b) | 0.093 | 0.083 | 0.082 | 0.073 |
| Yield (b-a) | −0.011 | −0.019 | −0.021 | −0.030 |
| Yield (b-a) (mol %)* | −5.0 | −9.1 | −9.9 | −14.4 |
| MBE (mol) | | | | |
| Feed Amount (a) | 0 | 0 | 0 | 0 |
| Resulting Amount (b) | 0.027 | 0.078 | 0.134 | 0.182 |
| Yield (b-a) | 0.027 | 0.078 | 0.134 | 0.182 |
| Yield (b-a) (mol %)* | 12.7 | 37.1 | 64.0 | 87.0 |
| Isobutylene | | | | |
| Feed Amount (mol) | 0.209 | 0.209 | 0.209 | 0.209 |

*Based on isobutylene.

EXAMPLE 2

The same procedures as described in Example 1 were conducted except using a mixture of 17.9 g of ethylene glycol di-tert-butyl ether and 24.8 g (0.210 mol) of ethylene glycol mono-tert-butyl ether in place of 17.9 g of ethylene glycol di-tert-butyl ether to obtain the results shown in Table 2. The MBE end product was produced in a high yield, and the net amount of DBE produced was zero or slightly minus.

TABLE 2

| | Reaction Temperature (°C.) | | | |
|---|---|---|---|---|
| | 45 | 60 | 75 | 90 |
| Ethylene glycol (mol) | | | | |
| Feed Amount (a) | 0.565 | 0.565 | 0.565 | 0.565 |
| Resulting Amount (b) | 0.535 | 0.447 | 0.380 | 0.371 |
| Yield (b-a) | −0.030 | −0.118 | −0.184 | −0.193 |
| Diisobutylene | | | | |
| Yield (mol) | 0.008 | 0.017 | 0.014 | 0.008 |
| DBE (mol) | | | | |
| Feed Amount (a) | 0.103 | 0.103 | 0.103 | 0.103 |
| Resulting Amount (b) | 0.097 | 0.101 | 0.102 | 0.103 |
| Yield (b-a) | −0.006 | −0.002 | −0.001 | 0.000 |
| Yield (b-a) | −2.9 | −1.1 | −0.5 | 0.000 |
| MBE (mol) | | | | |
| Feed Amount (a) | 0.210 | 0.210 | 0.210 | 0.210 |
| Resulting Amount (b) | 0.246 | 0.330 | 0.395 | 0.403 |
| Yield (b-a) | 0.036 | 0.120 | 0.185 | 0.193 |
| Yield (b-a) (mol %) | 17.2 | 57.5 | 88.7 | 92.4 |
| Isobutylene | | | | |
| Feed Amount (mol) | 0.209 | 0.209 | 0.209 | 0.209 |

COMPARATIVE EXAMPLE 1

The same procedures as described in Example 1 were conducted except using 24.8 g of ethylene glycol mono-tert-butyl ether in place of 17.9 g of ethylene glycol di-tert-butyl ether to obtain the results shown in Table 3. The yield of the MBE end product reached a maximum at about 65° to 70° C. Formation of the by-product of DBE was remarkable at about 60° C. or above.

TABLE 3

| | Reaction Temperature (°C.) | | | |
|---|---|---|---|---|
| | 45 | 60 | 75 | 90 |
| Ethylene Glycol (mol) | | | | |
| Feed Amount (a) | 0.565 | 0.565 | 0.565 | 0.565 |
| Resulting Amount (b) | 0.479 | 0.437 | 0.413 | 0.451 |
| Yield (b-a) | −0.086 | −0.128 | −0.152 | −0.113 |
| Diisobutylene | | | | |
| Yield (mol) | 0.004 | 0.011 | 0.010 | 0.009 |
| DBE (mol) | | | | |
| Feed Amount (a) | 0 | 0 | 0 | 0 |
| Resulting Amount (b) | 0.005 | 0.007 | 0.032 | 0.052 |
| Yield (b-a) | 0.005 | 0.007 | 0.032 | 0.052 |
| Yield (b-a) (mol %) | 2.5 | 3.2 | 15.1 | 24.7 |
| MBE (mol) | | | | |
| Feed Amount (a) | 0.210 | 0.210 | 0.210 | 0.210 |
| Resulting Amount (b) | 0.291 | 0.331 | 0.330 | 0.272 |
| Yield (b-a) | 0.081 | 0.121 | 0.120 | 0.062 |
| Yield (b-a) (mol %) | 38.6 | 58.0 | 57.7 | 29.6 |
| Isobutylene | | | | |
| Feed Amount (mol) | 0.209 | 0.209 | 0.209 | 0.209 |

COMPARATIVE EXAMPLE 2

The same procedures as in Example 1 were conducted except for using only ethylene glycol and isobutylene to obtain the results shown in Table 4. The yield of the end product of MBE reached a maximum at about 75° C.

TABLE 4

| | Reaction Temperature (°C.) | | | | |
|---|---|---|---|---|---|
| | 45 | 60 | 75 | 90 | 105 |
| Ethylene Glycol (mol) | | | | | |
| Feed Amount (a) | 0.565 | 0.565 | 0.565 | 0.565 | 0.565 |
| Resulting Amount (b) | 0.490 | 0.444 | 0.390 | 0.393 | |
| Yield (b-a) | −0.074 | −0.121 | −0.174 | −0.172 | |
| Diisobutylene | | | | | |
| Yield (mol) | 0.001 | 0.007 | 0.005 | 0.004 | |
| DBE (mol) | | | | | |
| Feed Amount (a) | 0 | 0 | 0 | 0 | 0 |
| Resulting Amount (b) | 0 | 0.001 | 0.006 | 0.020 | |
| Yield (b-a) | 0 | 0.001 | 0.006 | 0.020 | |
| Yield (b-a) (mol %) | 0.0 | 0.3 | 2.6 | 9.5 | |
| MBE (mol) | | | | | |
| Feed Amount (a) | 0 | 0 | 0 | 0 | 0 |
| Resulting Amount (b) | 0.074 | 0.120 | 0.169 | 0.152 | 0.106 |
| Yield (b-a) | 0.074 | 0.120 | 0.169 | 0.152 | 0.106 |
| Yield (b-a) (mol %) | 35.5 | 57.5 | 80.7 | 72.8 | 50.7 |
| Isobutylene | | | | | |
| Feed Amount (mol) | 0.209 | 0.209 | 0.209 | 0.209 | 0.209 |

EXAMPLES 3–5

The same procedures as in Example 1 were conducted using an autoclave (200 ml in content volume) equipped with a stirrer and reacting the starting materials under reaction conditions shown in Table 5. The results thus obtained are shown in Table 5.

TABLE 5

| | Example No. | | |
|---|---|---|---|
| | 3 | 4 | 5 |
| Reaction Temperature (°C.) | 90 | 90 | 60 |
| Reaction Time (hr) | 3 | 1 | 4 |
| Ethylene Glycol (mol) | | | |
| Feed Amount (a) | 0.555 | 0.565 | 0.565 |
| Resulting Amount (b) | 0.356 | 0.404 | 0.384 |
| Yield (b-a) | −0.199 | −0.161 | −0.181 |
| Diisobutylene | | | |
| Yield (mol) | 0 | 0.006 | 0.004 |
| DBE (mol) | | | |
| Feed Amount (a) | 0.051 | 0.067 | 0.043 |
| Resulting Amount (b) | 0.051 | 0.060 | 0.043 |
| Yield (b-a) | 0 | −0.007 | 0 |

TABLE 5-continued

| | Example No. | | |
|---|---|---|---|
| | 3 | 4 | 5 |
| Yield (b-a) (mol %) MBE (mol) | 0.0 | −3.4 | 0.0 |
| Feed Amount (a) | 0 | 0.104 | 0 |
| Resulting Amount (b) | 0.199 | 0.272 | 0.181 |
| Yield (b-a) | 0.199 | 0.168 | 0.181 |
| Yield (b-a) (mol %) Isobutylene | 95.2 | 81.6 | 87.0 |
| Feed Amount (mol) | 0.209 | 0.206 | 0.208 |

From the results of Examples 3 and 5, it is seen that the net amount of by-produced DBE can be maintained zero by adding only DBE through controlling of the DBE amount added, to thereby obtain MBE in a high yield.

In Example 4 the amounts of DBE and MBE added respectively were reduced about ½ as compared with Example 2. In this Example, too, enough effect of preventing formation of the by-product of DBE was observed, though the yield of MBE was slightly less than in Example 2.

Yields of MBE and DBE obtained in Examples 1 and 2 and Comparative Examples 1 and 2 and yields of MBE in Examples 3 to 5 are shown in the attached drawing.

EXAMPLE 6

100 ml of Amberlyst 15 previously swollen with ethylene glycol was charged in a stainless steel-made pressure-resistant pipe type reactor. A $C_4$ fraction obtained by naphtha cracking (isobutylene content: 45.0 wt%), ethylene glycol, and ethylene glycol di-tert-butyl ether were continuously fed to a catalyst bed under the reaction conditions of 75° C., 20 $kg/cm^2$. Linear velocity of the total starting materials and additive was 484 cm/hr. Reaction results of steady state which was attained five hours after initiation of the reaction are shown in Table 6. There was observed reduction in the amount of ethylene glycol di-tert-butyl ether.

COMPARATIVE EXAMPLE 3

Table 6 shows the results obtained by reacting in the same manner as in Example 6 except for adding no ethylene glycol di-tert-butyl ether to starting material. Unlike Example 6, ethylene glycol di-tert-butyl ether was by-produced.

Additionally, feed amounts, resulting amounts, and yields in Table 6 are presented as the amounts fed or produced in the unit of mmol per 1 hour per 1 ml of the catalyst.

TABLE 6

| | Example 6 | Comparative Example 3 |
|---|---|---|
| Reaction Temperature (°C.) | 75 | 75 |
| Ethylene Glycol | | |
| Feed Amount (a) | 22.50 | 22.50 |
| Resulting Amount (b) | 17.90 | 16.53 |
| Yield (b-a) | −4.60 | −5.97 |
| Diisobutylene | | |
| Yield | 0.05 | 0.05 |
| DBE | | |
| Feed Amount (a) | 1.04 | 0 |
| Resulting Amount (b) | 0.70 | 0.62 |
| Yield (b-a) | −0.34 | 0.62 |
| Yield (b-a) (mol %) MBE | −4.3 | 7.9 |
| Feed Amount (a) | 0 | 0 |
| Resulting Amount (b) | 4.94 | 5.35 |

TABLE 6-continued

| | Example 6 | Comparative Example 3 |
|---|---|---|
| Yield (b-a) | 4.94 | 5.35 |
| Yield (b-a) (mol %) Isobutylene | 62.7 | 67.9 |
| Feed Amount | 7.88 | 7.88 |

EXAMPLE 7

The reaction was conducted in the same manner as in Example 2 except for using as a catalyst 5.3 g of styrene sulfonic acid type strongly acidic cation-exchange resin, Amberlite IR-118 (made by Rohm & Haas Co.; gel type resin; total exchange capacity: 4.4 meq/g-dry resin; specific surface area: not more than 1 $m^2/g$) previously well dried at 120° C. under reduced pressure. Reaction conditions were 75° C. in reaction temperature and 1 hour in reaction time. Results of the reaction are shown in Table 7. As is seen in Table 7, the end product of ethylene glycol mono-tert-butyl ether was produced in a high yield, and the net amount of by-produced ethylene glycol di-tert-butyl ether was zero.

EXAMPLE 8

The reaction was conducted in the same manner as in Example 2 except for using 5.5 g of commercially available sulfonated coal, Dusarit S (made by Activit N.V.) as a catalyst and reacting for 3 hours. The reaction temperature was 75° C. Results thus obtained are shown in Table 7.

As is seen from Table 7, the yield of the end product of ethylene glycol mono-tert-butyl ether was high, and the net amount of ethylene glycol di-tert-butyl ether was slightly decreased.

TABLE 7

| | Example 7 | Example 8 |
|---|---|---|
| Reaction Temperature (°C.) | 75 | 75 |
| Reaction Time (hr) | 1 | 3 |
| Ethylene Glycol (mol) | | |
| Feed Amount (a) | 0.565 | 0.565 |
| Resulting Amount (b) | 0.381 | 0.390 |
| Yield (b-a) | −0.184 | −0.175 |
| Diisobutylene | | |
| Yield (mol) | 0.012 | 0.010 |
| DBE (mol) | | |
| Feed Amount (a) | 0.103 | 0.103 |
| Resulting Amount (b) | 0.103 | 0.102 |
| Yield (b-a) | 0.000 | −0.001 |
| Yield (b-a) (mol %) | 0.0 | −0.5 |
| MBE (mol) | | |
| Feed Amount (a) | 0.210 | 0.210 |
| Resulting Amount (b) | 0.394 | 0.386 |
| Yield (b-a) | 0.184 | 0.176 |
| Yield (b-a) (mol %) Isobutylene | 88.0 | 84.2 |
| Feed Amount (mol) | 0.209 | 0.209 |

EXAMPLE 9

3.30 g of Amberlyst 15 as a catalyst and, as starting materials, 22.1 g (0.356 mole) of ethylene glycol, 4.94 g (0.088 mole) of isobutylene, and as additives, 4.18 g (0.024 mole) of ethylene glycol di-tert-butyl ether, 1.39 g (0.077 mole) of water were charged in an autoclave (100 ml in volume) equipped with a stirrer rotating at 1,300 rpm, followed by charging nitrogen gas and reacting for 6 hours under a pressure of 20 $kg/cm^2$ at 75° C.

The result is shown in Table 8. MBE was produced in a high yield and the net amount of DBE produced was zero. The formation of tert-butyl alcohol was observed.

TABLE 8

| Reaction Temperature (°C.) | 75 |
|---|---|
| Reaction Time (hr) | 6 |
| Ethylene Glycol (mol) | |
| Feed Amount (a) | 0.356 |
| Resulting (b) | 0.297 |
| Yield (b-a) | −0.059 |
| Diisobutylene (mol) | |
| Yield | 0.000 |
| DBE (mol) | |
| Feed Amount (a) | 0.024 |
| Resulting Amount (b) | 0.024 |
| Yield (b-a) | 0.000 |
| Water (mol) | |
| Feed Amount | 0.077 |
| Isobutylene (mol) | |
| Feed Amount | 0.088 |
| MBE (mol) | |
| Feed Amount (a) | 0.000 |
| Resulting Amount (b) | 0.059 |
| Yield (b-a) | 0.059 |
| Tert-butyl Alcohol (mol) | |
| Yield | 0.013 |

While the invention has been described in detail and with reference to specific embodiments thereof, it will be apparent to one skilled in the art that various changes and modifications can be made therein without departing from the spirit and scope thereof.

What is claimed is:

1. In a process for producing ethylene glycol mono-tert-butyl ether by reacting ethylene glycol with isobutylene in the presence of a strongly acidic cation-exchange material, the improvement which comprises previously adding to the reaction system an additive comprising ethylene glycol di-tert-butyl ether and ethylene glycol mono-tert-butyl ether in a molar ratio of ethylene glycol di-tert-butyl ether to ethylene glycol mono-tert-butyl ether of about 1:0 to 1:5 in an amount such that said ethylene glycol di-tert-butyl ether is at least about 10 mol% based on the ethylene glycol or isobutylene, whichever is less, and conducting the reaction at reaction temperatures of about 60° to 130° C.

2. The process of claim 1, wherein said additive is a mixture of ethylene glycol di-tert-butyl ether and ethylene glycol mono-tert-butyl ether.

3. The process of claims 1 or 2, wherein a mixture of hydrocarbons having 4 carbon atoms and containing isobutylene is used as the isobutylene component reacted with the ethylene glycol.

4. The process of claims 1 or 2, wherein said catalyst is a sulfonated material.

5. The process of claims 1 or 2, wherein the molar ratio of ethylene glycol to isobutylene is about 1:0.1 to 1:10.

6. The process of claims 1 or 2, wherein ethylene glycol di-tert-butyl ether is added in an amount of about 30 to 80 mol% based on ethylene glycol or isobutylene, whichever is less.

7. The process of claims 1 or 2, wherein said reaction temperature is about 75° to 130° C.

8. The process of claims 1 or 2, wherein said reaction temperature is about 85° to 110° C.

9. The process of claims 1 or 2, wherein said reaction is conducted under atmospheric pressure.

10. The process of claims 1 or 2, wherein said reaction is conducted under an applied pressure.

11. The process of claims 1 or 2, wherein said reaction is conducted in a batchwise manner.

12. The process of claims 1 or 2, wherein said reaction is conducted in a continuous manner by passing the starting materials and additive through a fixed catalyst bed.

13. The process of claim 12, wherein said reaction is conducted by controlling the linear velocity of the starting materials to at least about 30 cm/hr.

14. The process of claim 1, wherein the molar ratio of ethylene glycol di-tert-butyl ether to ethylene glycol mono-tert-butyl ether in said mixture is about 1:0 to about 1:3.

15. The process of claim 4, wherein said cation-exchange material is a styrene sulfonic acid type cation-exchange resin, a phenolsulfonic acid type cation-exchange resin, a sulfonated coal, or a sulfonated asphalt.

16. The process of claim 1, wherein said reaction is carried out in the presence of diisobutylene, triisobutylene, or water.

* * * * *